(12) United States Patent
Sumiya

(10) Patent No.: US 7,749,216 B2
(45) Date of Patent: Jul. 6, 2010

(54) CORNEAL SURGERY APPARATUS

(75) Inventor: Toshifumi Sumiya, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 1128 days.

(21) Appl. No.: 11/200,008

(22) Filed: Aug. 10, 2005

(65) Prior Publication Data
US 2006/0084956 A1 Apr. 20, 2006

(30) Foreign Application Priority Data
Aug. 10, 2004 (JP) ............................. 2004-233560

(51) Int. Cl.
*A61F 9/008* (2006.01)
(52) U.S. Cl. ....................... 606/5; 606/4; 606/6; 607/88
(58) Field of Classification Search .................. 607/88; 606/4, 5, 6
See application file for complete search history.

(56) References Cited

U.S. PATENT DOCUMENTS

| | | | | |
|---|---|---|---|---|
| 5,633,694 | A | * | 5/1997 | Mihashi et al. ............. 351/211 |
| 5,963,300 | A | * | 10/1999 | Horwitz ....................... 351/209 |
| 6,159,202 | A | * | 12/2000 | Sumiya et al. ................. 606/4 |
| 6,585,723 | B1 | * | 7/2003 | Sumiya .......................... 606/5 |
| 6,702,806 | B2 | * | 3/2004 | Gray et al. ..................... 606/5 |
| 7,101,365 | B1 | * | 9/2006 | Sharon ........................... 606/9 |
| 2002/0133145 | A1 | * | 9/2002 | Gerlach et al. ................. 606/4 |
| 2003/0223037 | A1 | * | 12/2003 | Chernyak ..................... 351/209 |
| 2007/0049996 | A1 | * | 3/2007 | Black ........................... 607/89 |

FOREIGN PATENT DOCUMENTS

| | | |
|---|---|---|
| JP | A-9-149914 | 6/1997 |
| JP | A-2000-139996 | 5/2000 |
| JP | A-2003-79657 | 3/2003 |
| JP | A-2003-210514 | 7/2003 |
| JP | A-2004-28970 | 1/2004 |

* cited by examiner

*Primary Examiner*—Henry M Johnson, III
*Assistant Examiner*—Jeffrey B Lipitz
(74) *Attorney, Agent, or Firm*—Oliff & Berridge, PLC

(57) ABSTRACT

A corneal surgery apparatus capable of accurately measuring a three-dimensional corneal shape in a state of being subjected to corneal ablation. The apparatus has a unit including a laser source emitting a laser beam to bring about corneal ablation and a first optical system irradiating a cornea with the beam, a unit including a light source emitting measurement light with a wide wavelength band, a beam splitter dividing the light, a second optical system irradiating the cornea with one divided light, a movable reference mirror on an optical path of the other divided light and a photo-detector at a position photo-receiving interference light of the measurement light reflected by the cornea and the mirror, which obtains a three-dimensional corneal shape based on an interference light image, a unit obtaining corneal ablation data based on obtained corneal shape data, and a unit controlling the ablation unit based on the ablation data.

2 Claims, 4 Drawing Sheets

CORNEAL SURGERY APPARATUS

BACKGROUND OF THE INVENTION

1. Field of the Invention

The present invention relates to a corneal surgery apparatus for ablating a cornea with a laser beam to correct a refractive error of an eye.

2. Description of Related Art

Conventionally, there is known a corneal surgery apparatus for ablating corneal tissue by irradiating a cornea with a laser beam to correct a refractive error of an eye. There is also known a corneal topography apparatus (corneal shape measurement apparatus) for obtaining data on a corneal shape being the basis for data on corneal ablation.

Normally, corneal shape measurement is performed by the corneal topography apparatus while a patient is seated, and corneal ablation is performed by the corneal surgery apparatus while the patient lies on his/her back, so that it is often the case that the state of an eye of the patient at the time of the measurement and that at the time of the ablation are not the same. Therefore, when the corneal ablation data is to be found based on the corneal shape data obtained by the corneal topography apparatus, it is necessary to correct the data based on a comparison result between the states of the eye at the time of the measurement and at the time of the ablation.

SUMMARY OF THE INVENTION

An object of the invention is to overcome the problems described above and to provide a corneal surgery apparatus capable of accurately measuring a three-dimensional shape of a cornea in a state of being subjected to corneal ablation.

To achieve the objects and in accordance with the purpose of the present invention, a corneal surgery apparatus has a corneal ablation unit including a laser source which emits a laser beam to bring about ablation of a cornea and a first irradiation optical system for irradiating the cornea with the laser beam emitted from the laser source, a corneal shape measurement unit including a light source which emits measurement light with a wide wavelength band, a beam splitter which divides the measurement light emitted from the light source, a second irradiation optical system for irradiating the cornea with one of the divided measurement light, a reference mirror movable in a direction of an optical axis which is arranged on an optical path of the other one of the divided measurement light and a photo-detector which is arranged at a position to photo-receive interference light of the measurement light reflected by the cornea and the measurement light reflected by the reference mirror, which obtains a three-dimensional shape of the cornea based on an image formed by the interference light detected by the photo-detector, a calculation unit which obtains data on corneal ablation based on data on the obtained corneal shape, and a control unit which controls the corneal ablation unit based on the obtained corneal ablation data.

Additional objects and advantages of the invention are set forth in the description which follows, are obvious from the description, or may be learned by practicing the invention. The objects and advantages of the invention may be realized and attained by the corneal surgery apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 5A-1, 5A-2, 5B-1 and 5B-2 are views for illustrating the way to correct a positional deviation of the image.

DETAILED DESCRIPTION OF THE PREFERRED EMBODIMENTS

Figure 1:
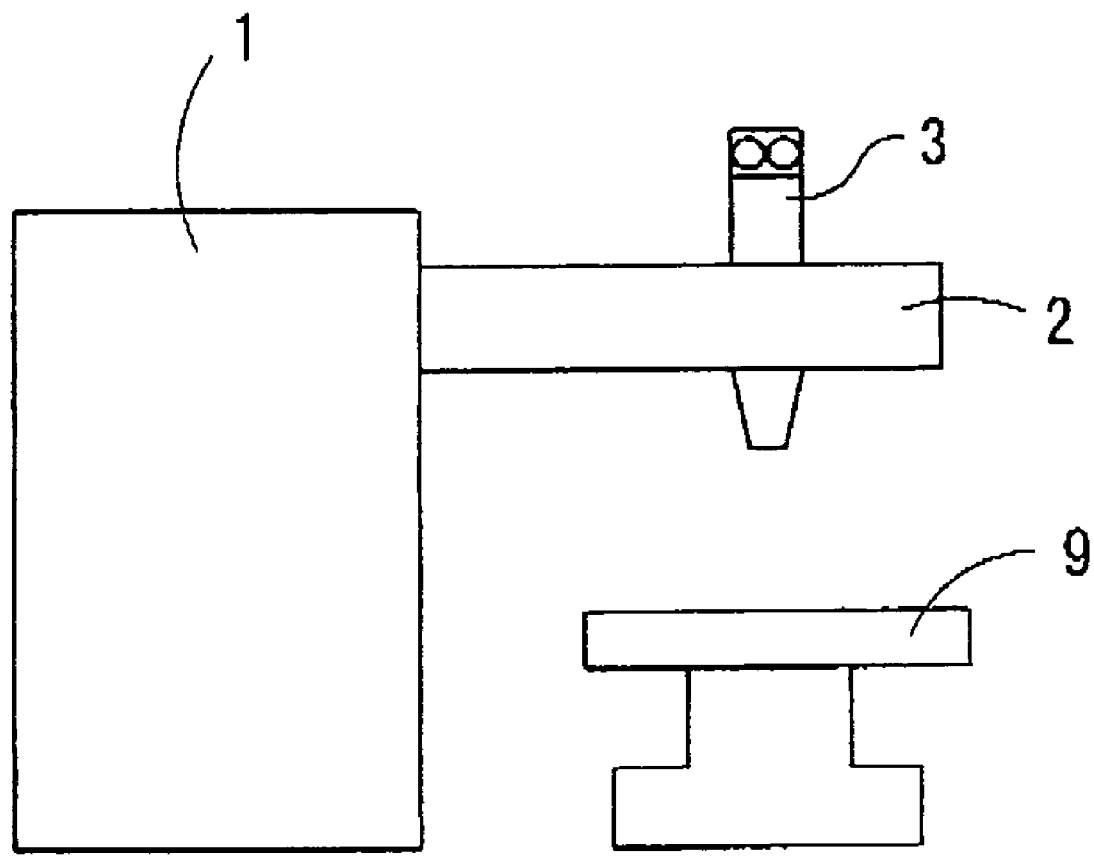
FIG. 1 is a view showing a schematic configuration of a corneal surgery apparatus consistent with one embodiment of the present invention.
Figure 2:
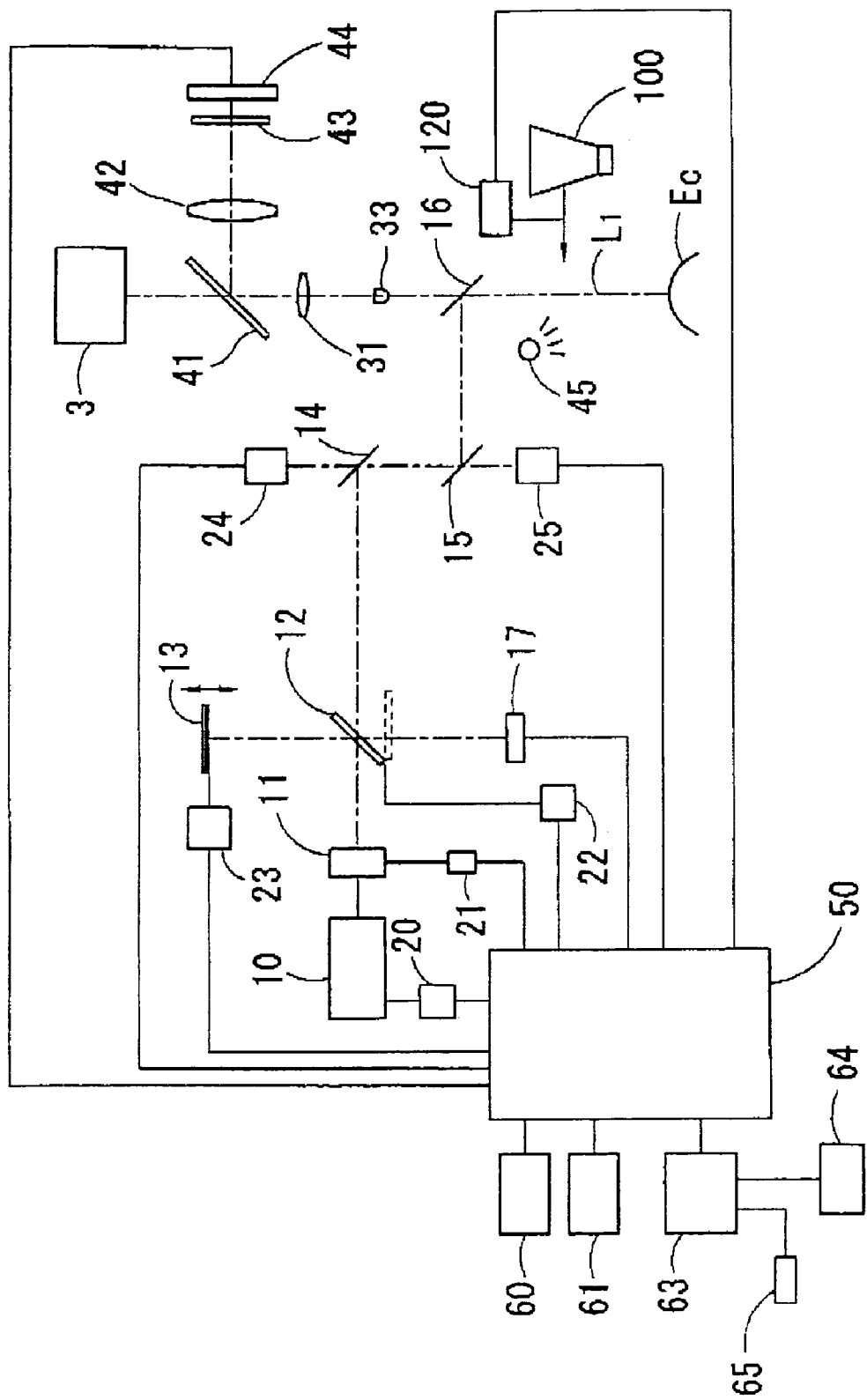
FIG. 2 is a view showing a schematic configuration of an optical system and a control system of the corneal surgery apparatus.

A detailed description of one preferred embodiment of a corneal surgery apparatus embodied by the present invention is provided below with reference to the accompanying drawings. FIG. 1 is a view showing a schematic configuration of a corneal surgery apparatus consistent with an embodiment of the present invention. FIG. 2 is a view showing a schematic configuration of an optical system and a control system of the corneal surgery apparatus. From a main body 1 of the apparatus, extending is an arm unit 2 which is movable in horizontal and vertical directions. Housed in the main body 1 and the arm unit 2 is the optical system to be described later. Further, mounted on the arm unit 2 is a binocular microscope unit 3 for observing an eye of a patient. The patient is laid on his/her back on a bed 9, and corneal shape measurement and corneal ablation are performed while the patient is kept in the position.

<Corneal Shape Measurement Optical System>

From a laser source 10, a laser beam (measurement light) for corneal shape measurement is emitted. In the present embodiment, a femtosecond laser source emitting an infrared ultrashort pulse laser beam with a wide wavelength band is used for the laser source 10, which is, for example, a titanium sapphire laser source emitting an ultrashort pulse laser beam having a center wavelength of about 800 nm. In addition, a pulse width of the laser beam is preferably from 10 femtoseconds to some tens of picoseconds (100 picoseconds) for example, 130 femtoseconds. Besides, for the light source for corneal shape measurement, it is possible to use an SLD (super luminescent diode) with a wavelength band of about 25 nm to allow resolution of about 10 to 15 μm; however, it is preferable to use the femtosecond laser source emitting the ultrashort pulse laser beam with the wide wavelength band since it allows resolution of about 1 μm.

A half mirror 12 is inserted into an optical path of the laser beam at the time of the corneal shape measurement to divide the laser beam from the laser source 10. A part of the laser beam transmitted through the half mirror 12 is reflected by scanning mirrors 14 and 15 which are oscillated by scanning-mirror oscillating units 24 and 25. The laser beam reflected by the scanning mirrors 14 and 15 is reflected by a dichroic mirror 16 having properties of reflecting the infrared laser beam emitted from the laser source 10 and transmitting visible light and infrared light emitted from an infrared light source 45 to be described later, and is irradiated on a cornea Ec of the patient's eye. The laser beam reflected by the cornea Ec is reflected by the dichroic mirror 16 and the scanning mirrors 15 and 14, and is divided by the half mirror 12, and the one reflected by the half mirror 12 enters a photo-detector 17.

On the other hand, the other part of the laser beam reflected by the half mirror 12 is reflected by a reference mirror 13 which is moved by a reference-mirror moving unit 23 in a direction of an optical axis L1 (in a direction of the arrow in the figure). The laser beam reflected by the reference mirror 13 is divided by the half mirror 12, and the one transmitted through the half mirror 12 enters the photo-detector 17.

Between the laser source 10 and the half mirror 12, a correcting optical system 11 is inserted, which corrects a beam diameter and energy density of the laser beam. The correcting optical system 11 brings the laser beam from the laser source 10 into a spot size (diameter) of about 10 μm on the cornea Ec.

<Corneal Ablation Optical System>

A corneal ablation optical system shares the laser source 10, the scanning mirrors 14 and 15, and the dichroic mirror 16 with the corneal shape measurement optical system. In contrast to the laser beam for corneal shape measurement, a laser beam for corneal ablation requires higher energy. Therefore, in the present embodiment, a laser source capable of emitting a laser beam of energy required for corneal ablation is used for the laser source 10, and at the time of the corneal shape measurement, output energy of the laser source 10 is lowered by a laser-source driving unit 20 and the energy density of the laser beam is corrected by the correcting optical system 11 having an attenuator. In addition, since a beam diameter required at the time of the corneal shape measurement is different from the one required at the time of the corneal ablation, the beam diameter is corrected by the correcting optical system 11. At the time of the corneal ablation, the correcting optical system 11 is removed from the optical path by a correcting-optical-system moving unit 21, and the half mirror 12 is removed from the optical path by a half-mirror moving unit 22. In addition, an irradiation end unit 100 is inserted into an optical path between the dichroic mirror 16 and the patient's eye by an irradiation-end-unit moving unit 120.

Figure 3:
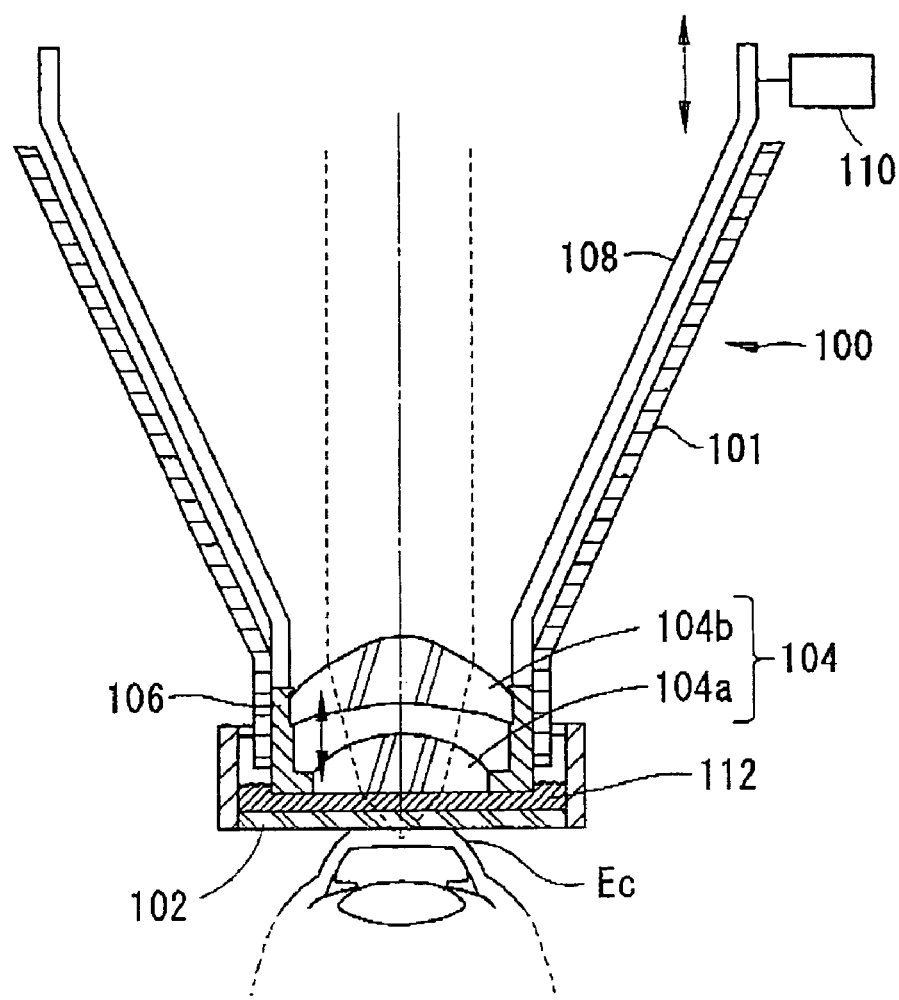
FIG. 3 is a view showing a schematic configuration of an irradiation end unit.

FIG. 3 is a view showing a schematic configuration of the irradiation end unit 100. At the end of a frame 101 of the irradiation end unit 100, held is a plate 102 with a flat undersurface which has a property of transmitting the infrared laser beam from the laser source 10 and the visible light. Arranged above the plate 102 is a collective optical system 104 including a first collective lens 104a and a second collective lens 104b with double aspherical surfaces. In order to collect the laser beam into a minute spot, the collective optical system 104 is made by combining a plurality of lenses to raise an NA (numerical aperture). In addition, the collective optical system 104 is attached to a lens holder 106 which is movable in the optical axis L1 direction. Mounted atop the lens holder 106 is a supporting member 108, which is moved slightly in the optical axis L1 direction by a collective-optical-system moving unit 110 mounted atop the irradiation end unit 100.

Further, interposed between the plate 102 and the lens 104a is a liquid 112 for refractive index adjustment. The liquid 112 has almost the same refractive index as that of a material constituting the lens 104a and the plate 102, raising the NA at a light-collecting point of the laser beam and decreasing losses due to reflection, so that adjustment of a light-collecting position is facilitated. By the collective optical system 104, the laser beam is collected into a minute spot inside the cornea Ec located beneath the plate 102. A spot size of the laser beam at the light-collecting point is preferably about 1 μm.

<Observation Optical System>

Above the dichroic mirror 16, an objective lens 31 and the binocular microscope unit 3 are arranged.

On a fixation lamp 33 arranged on the optical axis L1, the patient's eye is fixed at the time of the corneal shape measurement and the corneal ablation.

<Eye Position Detection Optical System>

The infrared light source 45 for anterior-eye-segment illumination emits the infrared light with a center wavelength of about 950 nm which is out of a wavelength range of the infrared laser beam from the laser source 10. The infrared light from the light source 45 reflected by an anterior segment of the patient's eye is transmitted through the dichroic mirror 16 to be reflected by a dichroic mirror 41, which has properties of reflecting the infrared light from the light source 45 and transmitting the visible light, and is transmitted through an image-pickup lens 42 and an infrared light transmission filter 43, which cuts light with wavelengths of no longer than 900 nm, to form an image on an image-pickup element 44 such as a CCD camera.

<Control System>

Output from the image-pickup element 44 and output from the photo-detector 17 are inputted into a control unit 50. Besides, the control unit 50 is connected with units such as the laser-source driving unit 20, the correcting-optical-system moving unit 21, the half-mirror moving unit 22, the reference-mirror moving unit 23, the scanning-mirror oscillating units 24 and 25, the collective-optical-system moving unit 110, the irradiation-end-unit moving unit 120, an arm moving unit 60 for moving the arm unit 2 in a three-dimensional direction, an input unit 61 for inputting various instruction signals for the apparatus, and a calculation unit 63 for calculating data on corneal shape, data on corneal ablation and the like. In addition, the calculation unit 63 is connected with a display unit 64, an input unit 65 and the like.

Hereinafter, operations of the corneal surgery apparatus having the above configuration will be described. First, an operation mode of the apparatus is set into a corneal shape measurement mode using a mode changeover switch in the input unit 61. When the corneal shape measurement mode is established, the irradiation end unit 100 is removed from the optical path, and the correcting optical system 11 and the half mirror 12 are inserted into the optical path.

Next, while the anterior segment of the patient's eye is observed via the microscope unit 3, which is illuminated with the visible light from an unillustrated visible light source for anterior-eye-segment illumination, the arm unit 2 is moved in the three-dimensional direction using an arm moving switch in the input unit 61 to make an alignment so that an unillustrated reticle arranged in the microscope unit 3 and a position of the pupil center of the patient's eye have a predetermined positional relationship.

Upon completion of the alignment, the corneal shape measurement is started. At the time of the corneal shape measurement, the output energy of the laser source 10 is lowered by the driving unit 20, and further, attenuated by the correcting optical system 11 so as to correct the beam diameter specifically for measurement. The laser beam from the laser source 10 is divided by the half mirror 12. The laser beam transmitted through the half mirror 12 is scanned on the cornea Ec in a two-dimensional direction (X- and Y-directions) by oscillation of the scanning mirrors 14 and 15, and the laser beam reflected by the half mirror 12 is reflected by the reference mirror 13.

The laser beam reflected by the cornea Ec enters the half mirror 12 via the dichroic mirror 16 and the scanning mirrors 14 and 15 while the laser beam reflected by the reference mirror 13 also enters the half mirror 12, and the laser beams enter the photo-detector 17 as interference light. When the two laser beams entering the photo-detector 17 have the same optical path lengths, they reinforce each other by interference to be detected as an interference signal by the photo-detector 17. However, when the two laser beams entering the photo-detector 17 do not have the same optical path lengths, they cancel each other out not to be detected as an interference signal by the photo-detector 17. Hence, the optical path length on the part of the reference mirror 13 is changed by moving the reference mirror 13 in the optical axis L1 direction. When the optical path lengths of the laser beam reflected by a surface (anterior or posterior surface) of the cornea Ec and the laser beam reflected by the reference mirror 13 become the same, the laser beams are detected as the interference signal by the photo-detector 17, and thereby intensity distribution of the cornea Ec in a height direction (Z-direction) may be obtained.

Figure 4:
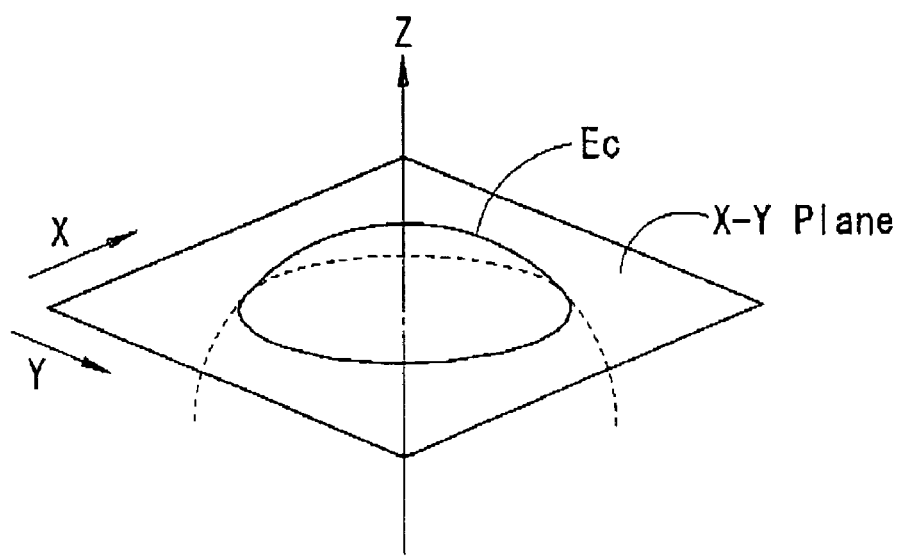
FIG. 4 is a view for illustrating an example of the way to obtain an image on an X-Y plane by scanning measurement light in a two-dimensional direction.

Scanning the laser beam in the two-dimensional direction by the scanning mirrors 14 and 15 allows an image of the interference signal in an X-Y plane to be obtained (see FIG. 4), and based on intensity distribution of this image, positions of surface portions at respective points on the cornea Ec may be detected. Then, the reference mirror 13 is moved in the optical axis L1 direction to obtain images at respective travel positions, allowing a three-dimensional shape of the cornea Ec to be obtained (constructed).

Here, resolution in a depth direction may be increased since the laser beam with the wide wavelength band is used for the light for corneal shape measurement. In the case of interference by light with a narrow wavelength band such as monochromatic light, where waves of approximately the same wavelengths are overlapping, sinusoidal fringes of light and shade occur over a long optical path difference. In contrast, in the case of the interference by the light with the wide wavelength band, where waves of different wavelengths are overlapping, interference fringes cancel each other out in an area deviated from the optical path difference, and they appear only in a range where a coherence length is short. Therefore, especially using an ultrashort pulse laser beam allows resolution up to about 1 μm to be obtained.

Detection signals sent from the photo-detector 17, position signals of the reference mirror 13 sent from the moving unit 23, and position signals of the scanning mirrors 14 and 15 sent from the oscillating units 24 and 25 are inputted into the calculation unit 63 via the control unit 50. Based on these signals, the calculation unit 63 obtains the three-dimensional shape of the cornea Ec. The obtained corneal shape includes a posterior surface shape as well as an anterior surface shape, so that corneal thickness is also obtained from both the shapes.

Incidentally, at the time of the corneal shape measurement, a position of the patient's eye is detected at the same time. That is to say, a signal of the anterior-eye-segment image sent from the image-pickup element 44 is inputted into the calculation unit 63 via the control unit 50, and the calculation unit 63 subjects the anterior-eye-segment image to image-processing to detect the position of the patient's eye. In the case of constructing the three-dimensional shape of the cornea Ec based on the two-dimensional image and travel positions of the reference mirror 13, a deviation of the position of the patient's eye causes the image to deviate in the X- and Y-directions, so that it is preferable to correct the positional deviation of the image.

Figure 5:
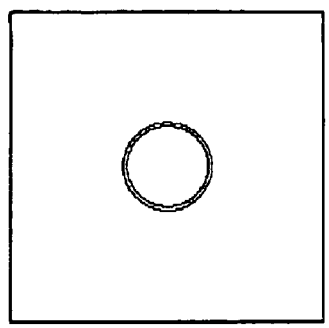
Figure 5:
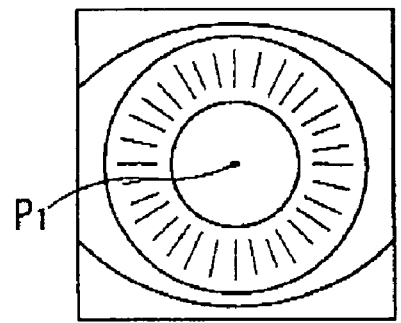
Figure 5:
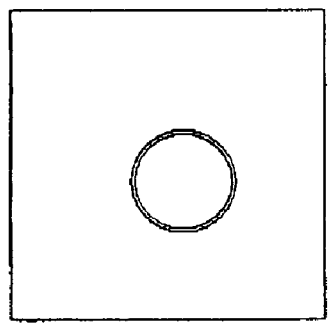
Figure 5:
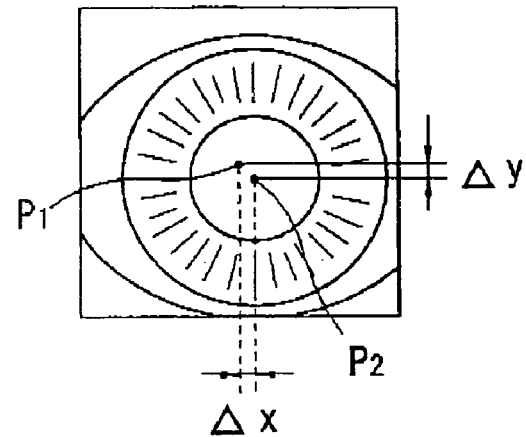

FIGS. 5A-1, 5A-2, 5B-1 and 5B-2 are views for illustrating the way to correct the positional deviation of the image. FIGS. 5A-1 and 5A-2 show examples of the images respectively obtained when the reference mirror 13 is at different positions. FIG. 5B-1 shows an anterior-eye-segment image obtained concurrently with the image of FIG. 5A-1, and FIG. 5B-2 shows an anterior-eye-segment image obtained concurrently with the image of FIG. 5A-2. For example, by obtaining the position of the pupil center and based on a result thereof, the positional deviation of the eye is detected. It is assumed that a positional deviation ($\Delta x$, $\Delta y$) of a pupil center position P2 obtained from the anterior-eye-segment image of FIG. 5B-2 with respect to a pupil center position P1 obtained from the anterior-eye-segment image of FIG. 5B-1 is detected. In this case, a position of the image of FIG. 5A-2 is corrected for the positional deviation ($\Delta x$, $\Delta y$) with respect to the image of FIG. 5A-1, and thereby more accurate data on the corneal shape is obtained. Besides, when the positional deviation of the eye becomes large, the control unit 50 may control to drive the arm moving unit 60 and move the arm unit 2 according to the positional deviation.

The obtained corneal shape data is displayed on the display unit 64 in the form of a color map and the like. Based on the obtained corneal shape data and data on a surgical condition inputted by the input unit 65, the calculation unit 63 calculates data on corneal ablation. The obtained corneal ablation data is also displayed on the display unit 64 in the form of a color map and the like.

Figure 6:
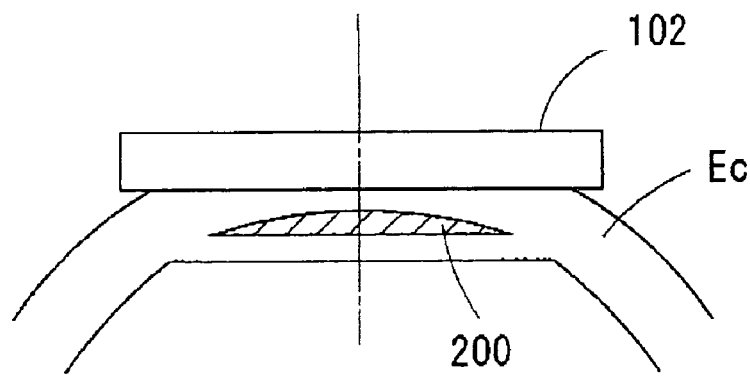
FIG. 6 is a view for illustrating an example of the way to ablate tissue inside a cornea.

The corneal ablation data being obtained, the operation mode of the apparatus is set into a corneal ablation mode using the mode changeover switch in the input unit 61. When the corneal ablation mode is established, the correcting optical system 11 and the half mirror 12 are removed from the optical path, and the irradiation end unit 100 is inserted into the optical path to be disposed at a predetermined position. At the time of the corneal ablation, while the anterior segment of the patient's eye is observed via the microscope unit 3, the arm unit 2 is moved in the three-dimensional direction to make an alignment so that the reticle and the pupil center position of the patient's eye have a predetermined positional relationship. In addition, the plate 102 is brought into contact with the cornea Ec to make the surface thereof flat. Thereafter, when an instruction signal for laser irradiation is inputted by the input unit 61, the control unit 50 controls the driving unit 20 to drive the laser source 10 to emit the laser beam and controls the oscillating units 24 and 25 and the moving unit 110 based on the corneal ablation data. For example, a spot position of the laser beam is controlled three-dimensionally so as to ablate internal tissue 200 of the cornea Ec, as shown in FIG. 6.

Besides, for the scanning of the laser beam by the scanning mirrors 14 and 15, raster scanning or spiral scanning may be employed. The depth direction is controlled by a travel position of the collective optical system 104. With the use of the ultrashort pulse laser beam, the laser beam may pass through the inside of the corneal tissue to collect in a very narrow region inside the cornea, so that only a portion with high energy density may be selectively used for ablation (i.e., internal reforming) by multi-photon absorption. Then, as the internal tissue 200 indicated by a shaded area in FIG. 6 is ablated, a curvature of the surface of the cornea Ec and refractive power of the cornea Ec may be changed.

Incidentally, for the method of the corneal ablation, another method may be employed, by which a flap is made by the collection of the laser beam using the collective optical system 104, the infrared laser beam from the laser source 10 is converted to an ultraviolet laser beam by a wavelength converter, the spot size is enlarged by removing the collective optical system 104 from the optical path, and the laser beam is superposed by scanning so as to ablate the corneal tissue.

Additionally, for the corneal shape measurement optical system for obtaining the three-dimensional shape of the cornea, another optical system in which polarization-sensitive optical coherence tomography is used may be employed. The corneal shape measurement optical system using the polarization-sensitive optical coherence tomography includes a ½ wavelength plate, a ¼ wavelength plate, a beam splitter such as a half mirror, a reference mirror, a diffraction grating which causes the measurement light reflected by the cornea and the measurement light reflected by the reference mirror to interfere with each other, a photo-detector arranged at a position to photo-receive the interference light, and the like. This optical system obtains an image by retrieving a signal which is based on a polarization component the same as that of the measurement light reflected by the reference mirror among the measurement light reflected by the cornea, and based on the obtained image, obtains a three-dimensional shape of the cornea. To the polarization-sensitive optical coherence tomography, the art disclosed in Japanese Patent Application Unexamined Publication No. 2004-28970 is applicable.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A corneal surgery apparatus comprising:
    a laser source which emits an ultrashort pulse laser beam with a wide wavelength band;
    an irradiation optical system for dividing the laser beam emitted from the laser source into measurement light and reference light by using a dividing and combining mirror, collecting the measurement light into a spot of a given size and irradiating a cornea with the measurement light, combining the measurement light reflected by the cornea and the reference light reflected by a reference mirror by using the dividing and combining mirror, and guiding the combined light to a photo-detector and obtaining an interference signal, the irradiation optical system comprising a scanning unit for two-dimensionally scanning the measurement light to be irradiated onto the cornea;
    a changeover switch for switching between a measurement mode of measuring a three-dimensional shape of the cornea and a surgery mode of ablating the cornea;
    a control unit that, when in the surgery mode, removes the dividing and combining mirror from an optical path of the irradiation optical system, inserts a correction optical system which changes the spot size into the optical path, and increases an output of the laser beam;
    an eye position detection unit which detects a positional deviation of an eye of a patient by detecting a pupil; and
    a calculation unit that, when in the measurement mode, obtains the three-dimensional shape of the cornea based on a detection signal from the photo-detector, positional information of the scanning unit, and positional information of the reference mirror.

2. The corneal shape measurement apparatus according to claim 1, wherein the calculation unit obtains a three-dimensional shape of an anterior surface of the cornea and a three-dimensional shape of a posterior surface of the cornea.

\* \* \* \* \*